(12) United States Patent
Thomas, III

(10) Patent No.: US 7,366,992 B2
(45) Date of Patent: Apr. 29, 2008

(54) METHOD AND SYSTEM FOR DISPLAYING AND/OR MANIPULATING MEDICAL IMAGE DATA

(75) Inventor: Lewis J. Thomas, III, Palo Alto, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 819 days.

(21) Appl. No.: 10/666,604

(22) Filed: Sep. 19, 2003

(65) Prior Publication Data

US 2005/0074157 A1   Apr. 7, 2005

(51) Int. Cl.
G06F 3/048 (2006.01)

(52) U.S. Cl. .................... 715/764; 709/217; 705/3; 382/132; 382/305

(58) Field of Classification Search ............. 715/764; 709/217; 705/3; 382/132, 305
See application file for complete search history.

(56) References Cited

U.S. PATENT DOCUMENTS

| | | | |
|---|---|---|---|
| 5,452,416 A | | 9/1995 | Hilton et al. |
| 5,513,101 A | | 4/1996 | Pinsky et al. |
| 5,603,323 A | | 2/1997 | Plugrath et al. |
| 5,715,823 A | * | 2/1998 | Wood et al. ............... 600/437 |
| 5,790,977 A | | 8/1998 | Ezekiel |
| 5,838,906 A | * | 11/1998 | Doyle et al. ............. 715/501.1 |
| 5,920,317 A | * | 7/1999 | McDonald ................. 715/853 |
| 6,014,689 A | | 1/2000 | Budge et al. |
| 6,049,671 A | | 4/2000 | Slivka et al. |
| 6,078,951 A | * | 6/2000 | Pashupathy et al. ........ 709/217 |
| 6,101,407 A | * | 8/2000 | Groezinger ................ 600/407 |
| 6,289,115 B1 | * | 9/2001 | Takeo ........................ 382/130 |
| 6,347,398 B1 | | 2/2002 | Parthasarathy et al. |
| 6,519,632 B1 | * | 2/2003 | Brackett et al. ............ 709/219 |
| 6,859,288 B1 | * | 2/2005 | Brackett et al. ........... 358/1.15 |
| 6,954,802 B2 | * | 10/2005 | Sutherland et al. ............ 710/5 |
| 6,963,673 B1 | * | 11/2005 | Patel et al. ................ 382/305 |
| 2002/0019751 A1 | * | 2/2002 | Rothschild et al. ............ 705/3 |
| 2002/0091659 A1 | * | 7/2002 | Beaulieu et al. ............. 706/62 |
| 2002/0109735 A1 | * | 8/2002 | Chang et al. ............... 345/853 |

(Continued)

OTHER PUBLICATIONS

"Philips prepares to launch system upgrade capable of true real-time 3D echo," Diagnostic Imaging Scan—The Global Biweekly of Medical Imaging, vol. 16, No. 18, CMP Media LLC, 2 pages (Sep. 11, 2002).

(Continued)

*Primary Examiner*—Weilun Lo
*Assistant Examiner*—TuyetLien Tran

(57) ABSTRACT

In one embodiment, a medical image viewer in compliance with a medical image standard is provided, and a file in compliance with the medical image standard is provided to the medical image viewer. The medical image standard specifies a first field for data not in compliance with the medical image standard and a second field for data in compliance with the medical image standard. The first field of the file comprises medical image data, and the second field of the file comprises information that can be used to obtain software to at least one of display and manipulate the medical image data. The software is obtained, and at least one of the following is performed with the software: displaying the medical image data and manipulating the medical image data. Other embodiments are provided, and each of the embodiments described herein can be used alone or in combination with one another.

19 Claims, 2 Drawing Sheets

U.S. PATENT DOCUMENTS

2003/0097351 A1* 5/2003 Rothschild et al. ............ 707/1
2003/0179917 A1* 9/2003 Faber et al. ................ 382/130
2004/0071038 A1* 4/2004 Sterritt ....................... 365/232
2005/0025349 A1* 2/2005 Crewe ........................ 382/128
2005/0244041 A1* 11/2005 Tecotzky et al. ............ 382/128

OTHER PUBLICATIONS

"LOGIQ 9," TruScan Imaging Technology, GE Medical Systems, 12 pages (2002).

"Driven by TruScan," http:\www.gemedicalsystems.com, 3 pages (printed Aug. 2003).

"DICOM Cook Book for Implementations in Modalities," Chapters 1 and 2, Version 1.1, Philips Medical Systems, 57 pages (Jan. 14, 1997).

* cited by examiner

METHOD AND SYSTEM FOR DISPLAYING AND/OR MANIPULATING MEDICAL IMAGE DATA

BACKGROUND

Digital Imaging and Communications in Medicine (DICOM) is a medical image standard for communication of biomedical diagnostic and therapeutic information in disciplines that use digital images and associated data. By using a medical image standard such as DICOM, medical image data can be shared and used among compliant devices, such as imaging systems and workstations. A typical use of DICOM is with two-dimensional ("2D") ultrasound images that are archived as a simple sequence of video images. Because the image data is typically processed, post-scan converted data, once 2D ultrasound images are stored, none of the post-processing capabilities normally available on the ultrasound system (such as gray-scale maps, edge enhancement, and video filters) are available to enhance the 2D image. This provides the benefit of ensuring that the archived image reproduces as closely as possible what the clinician who stored the image was viewing at the time the image was archived.

Recent advances have generated a desire to store and later manipulate other forms of image data. For example, in the emerging field of real-time three-dimensional ("3D") imaging (sometimes referred to as 4D, or Live-3D), clinicians would like to be able to apply post-processing functions to archived images, such as extracting a 2D image from a three-dimensional data set (i.e., multi-planer reconstruction ("MPR")) and viewing a 3D image from different angles. In addition to these 3D-specific post-processing functions, clinicians would also like to apply conventional 2D functions, such as gray-scale remapping, edge enhancement, and speckle reduction, to 3D images.

Although DICOM-compliant image viewers are not capable of displaying and/or manipulating these other forms of image data, the "private attribute" field in DICOM can be used to transmit non-standard image data from one DICOM device to another. Many ultrasound system manufacturers have taken advantage of this field to transmit data that cannot be stored in the DICOM format from a DICOM-compliant ultrasound system to a DICOM-compliant workstation. The workstation may have proprietary software installed to enable the workstation to utilize this non-DICOM data, or the workstation may simply ignore the non-DICOM data.

SUMMARY

The present invention is defined by the following claims, and nothing in this section should be taken as a limitation on those claims.

By way of introduction, the embodiments described below relate to methods and systems for displaying and/or manipulating medical image data. In one embodiment, a medical image viewer in compliance with a medical image standard is provided, and a file in compliance with the medical image standard is provided to the medical image viewer. The medical image standard specifies a first field for data not in compliance with the medical image standard and a second field for data in compliance with the medical image standard. The first field of the file comprises medical image data, and the second field of the file comprises information that can be used to obtain software to at least one of display and manipulate the medical image data. The software is obtained, and at least one of the following is performed with the software: displaying the medical image data and manipulating the medical image data. Other embodiments are provided, and each of the embodiments described herein can be used alone or in combination with one another.

The embodiments will now be described with reference to the attached drawings.

DETAILED DESCRIPTION OF THE PRESENTLY PREFERRED EMBODIMENTS

By way of introduction, the embodiments described below relate generally to diagnostic medical images. Although any type of medical image can be used, these embodiments will be illustrated in conjunction with ultrasound images. As noted in more detail below, other types of medical images can be used, and the following claims should not be limited to ultrasound images unless explicitly recited therein.

Figure 1:
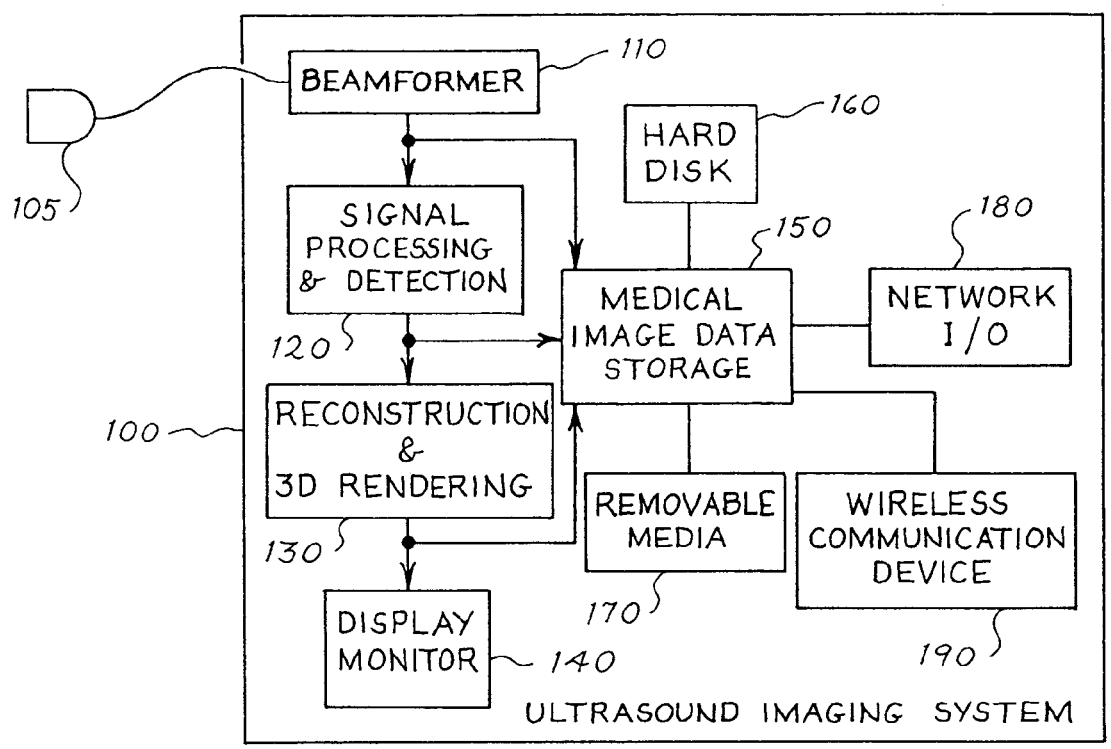
FIG. 1 is a block diagram of a medical diagnostic ultrasound imaging system of an embodiment.

Turning now to the drawings, FIG. 1 is a block diagram of an ultrasound system 100 of an embodiment. The ultrasound system 100 comprises a transducer probe 105, a beamformer 110, a signal processing and detection component 120, a reconstruction and 3D rendering component 130, and a display monitor 140. The ultrasound system 100 also comprises a medical image data storage component 150, which can capture image data at one or more locations along the image path, a hard disk 160, removable media 170 (e.g., a CD, an MO disk, etc.), a network I/O port 180, and a wireless communication device 190. The various components 110, 120, 130, 150 in the ultrasound system 100 can be implemented with dedicated hardware devices and/or one or more processors running software.

It is important to note that different ultrasound systems can be configured differently from the one shown in FIG. 1. For example, while the medical image data storage component 150 in the ultrasound system 100 in FIG. 1 is shown as being capable of capturing image data at three locations in the image path, medical image data storage components in other ultrasound imaging systems can be designed to capture image data at only one or two of the shown locations or at a different location in the image path not shown in FIG. 1. As another example, although there are three data output components shown in FIG. 1 (removable media 170, the network I/O 180, and the wireless communication device 190), more or fewer or different components can be used to export image data.

During an ultrasound examination, a sonographer contacts the transducer probe 105 with a patient, and the beamformer 110 applies a voltage to the transducer 105 to cause it to vibrate and emit an ultrasonic beam into the portion of the patient's body in contact with the transducer 105. Ultrasonic energy reflected from the patient's body impinges on the transducer 105, and the resulting voltages created by the transducer 105 are received by the beamformer 110. The beamformer 110 produces image data referred to as "RF data" and sends this image data to the signal processing and detection component 120. The signal processing and detection component 120 is used to at least detect the amplitude of the beamformer output and provide this amplitude to the reconstruction and rendering component. In addition to this amplitude detection, the signal processing and detection component may also be used to filter the signal in both range and lateral dimensions (azimuth for a one-dimensional transducer, azimuth and elevation for a two dimensional transducer), as well as providing the capability to synthesize signals by combining signals from more than one transmit event before amplitude detection and a compounding capability by combining signals from more than one transmit event after amplitude detection. The image data outputted by the signal processing and detection component 120 is provided to the reconstruction and 3D rendering component 130, which is where the echo amplitude data is converted into an image format such as a two-dimensional video frame (2D reconstruction) or is reconstructed into a three-dimensional volume data set (3D reconstruction) and then processed for display (3D rendering).

The medical image data storage component 150 captures image data from one or more points along the image path. The term "image data" refers to any data along the image path from the transducer probe 105 to the display monitor 140. Most ultrasound systems capture image data after the reconstruction and 3D rendering component 130. This data, which is DICOM compliant, consists only of 2D images or 2D renderings of 3D data. The image data outputted by the signal processing and detection component 120 could be 2D image data or 3D image data before scan conversion or reconstruction. This image data is not readable by DICOM-compliant devices such as DICOM workstations. Further, although current commercial ultrasound systems do not store radio frequency (RF) data due to storage capacity and network bandwidth limitations, the embodiments described herein can be used with RF data. Also, while FIG. 1 shows the medical image data storage component 150 capable of capturing image data at three points in the image path, the medical image data storage component 150 can be designed to capture image data at fewer or more points. The captured image data can be stored in the ultrasound system's hard disk 160 and/or removable media 170. The captured image data can also be exported from the ultrasound system 100 via the network I/O 180 (e.g., across an intranet or the Internet) or via the wireless communication device 190.

The ultrasound system 100 operates in compliance with a medical image standard and sends captured medical image data to another device operating in compliance with the medical image standard. In general, a medical image standard specifies the format of archiving and transmitting image data. A medical image standard can also specify the behavior of software when it encounters an image file in a format in compliance with the standard. Although any medical image standard now existing or developed in the future can be used, the DICOM standard will be used to illustrate this embodiment. In operation, the medical image data storage component 150 packages the medical image data in a file that is sent to a medical image viewer via removable media 170, the network I/O 180, or the wireless communication device 190. As used herein, the term "medical image viewer" broadly refers to any device that can be used to view and/or manipulate medical image data. Examples of medical image viewers include, but are not limited to, dedicated workstation (i.e., image review stations), general-purpose computers, personal digital assistants, cell phones, and set-top boxes. A medical image viewer can also be a medical imaging system (e.g., an ultrasound system) different from the one used to generate the medical image data.

Figure 2:
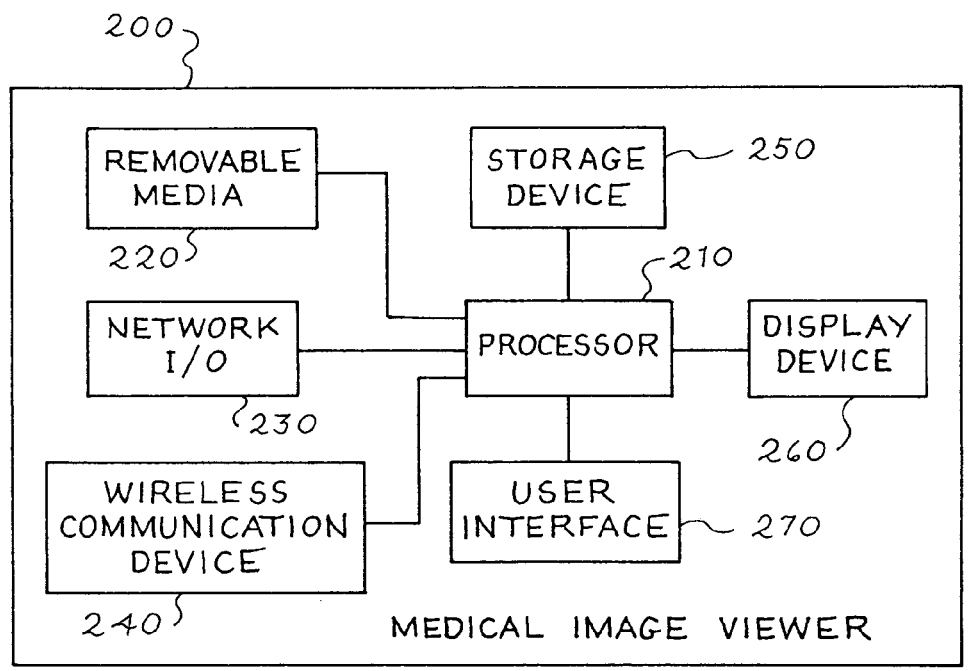
FIG. 2 is a block diagram of a medical image viewer of an embodiment.

FIG. 2 is a block diagram of a medical image viewer 200 of an embodiment. As shown in FIG. 2, the medical image viewer 200 comprises a processor 210 in communication with removable media 220, a network I/O 230, and a wireless communication device 240 that interfaces with the ultrasound system's removable media 170, network I/O 180, and a wireless communication device 190, respectively. The medical image viewer 200 also comprises a storage device 250 that can store the transferred medical image data file (and/or computer-readable program code executable by the processor 210), a display device 260, and a user interface 270.

Because the ultrasound system 100 and medical image viewer 200 operate in compliance with the same medical image standard, medical image data that is in compliance with the medical image standard can be viewed by the medical image viewer 200 (i.e., the processor 210 of the medical image viewer 200 runs medical-image-standard-compliant viewing software). With this embodiment, the medical image viewer 200 can also display and/or manipulate medical image data that is not in compliance with the medical image standard (e.g., RF data, pre-scan converted data, pre-reconstruction data, and a three-dimensional data set). This embodiment achieves this by incorporating capabilities and information required for viewing and/or manipulating medical images into the image data file sent to the medical image viewer 200. This will be discussed in more detail with reference to FIG. 3.

Figure 3:
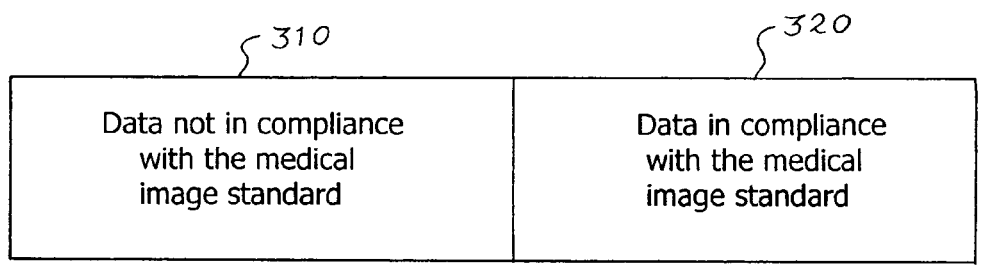
FIG. 3 is an illustration of a medical image standard of an embodiment.

As shown in FIG. 3, the medical image standard specifies that a file associated with medical image data have a first field 310 and a second field 320 (the medical image standard can also specify additional fields not shown in FIG. 3 for simplicity). The first field 310 is for data that is not in compliance with the medical image standard, and the second field 320 is for data that is in compliance with the medical image standard. In the DICOM medical image standard, the first field 310 is the DICOM private attribute, and the second field 320 is the DICOM standard attribute. The first field 310 comprises the non-compliant medical image data, and the second field 320 comprises information that can be used to obtain software to display and/or manipulate the medical image data stored in the first field 310. As used herein, the phrase "information that can be used to obtain software" broadly refers to any information that can be used to manually or automatically obtain software that can be executed on the processor 210 of the medical image viewer 200 to display and/or manipulate the medical image data in the first field 310.

Figure 4:
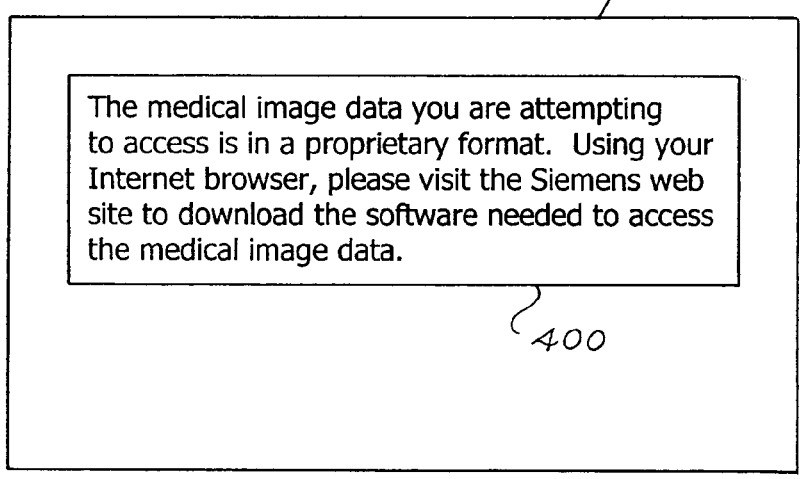
FIG. 4 is an illustration of a display device displaying a message of an embodiment instructing a user of a medical image viewer how to obtain software.
Figure 5:
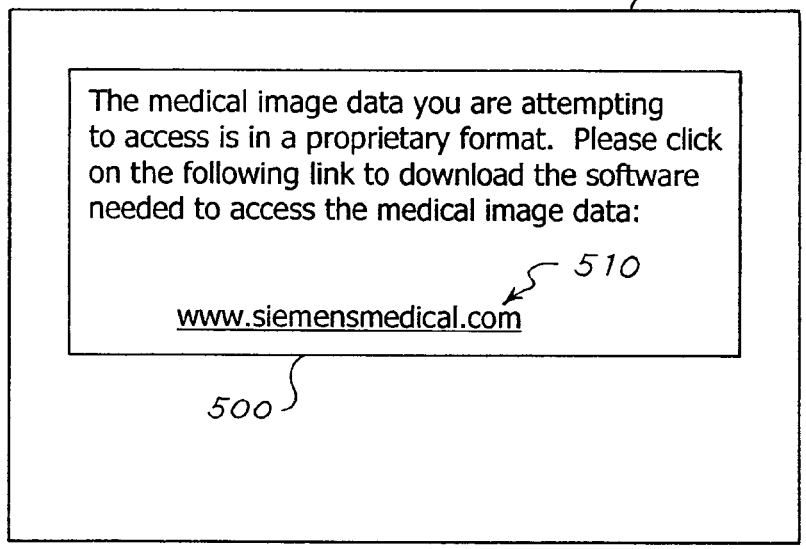
FIG. 5 is an illustration of a display device displaying a link of an embodiment to a network location storing software.

One example of such information is a message that instructs a user of the medical image viewer 200 how to obtain the software. When the file is received by the medical image viewer 200, the medical-image-standard-compliant software reads the data in the second field 320 and displays the data on the display device 260. As shown in FIG. 4, one suitable message 400 can be "The medical image data you are attempting to access is in a proprietary format. Using your Internet browser, please visit the Siemens web site to download the software needed to access the medical image data." In response to this message, the user can execute his Internet browser, which can be a separate application from the medical-image-standard-compliant software, to download the required software. The advantage of this approach is that it does not require any new special capability from the DICOM workstation. In this way, instructions on how to obtain proprietary software can be stored without having to have any special capabilities on the workstation. To save the user time, the information in the second field can comprise a link to a network location storing the software. For example, as shown in FIG. 5, the message 500 displayed to the user can include a link 510 that, when selected by the user, will cause the medical-image-standard-compliant software or Internet browser to download the software. As a further time-savings measure, the information in the second field can be computer-instruction code that automatically causes the medical-image-standard-compliant software or the Internet browser to download the needed software. While the term "Internet" has been used in these examples, it should be noted that the software can be stored on an intranet location, such as on a local server in a hospital intranet. These approached may require an extension to the DICOM standard.

If network resources are not available (e.g., when the medical image viewer 200 is not connected to a network and receives medical image data files via removable media 220), the information in the second field 320 can be a message informing the user of a telephone number, fax number, or postal address to which a verbal or written request for the software can be made. In yet another alternative, the required software can be resident on the medical image viewer 200 in a hidden form, and the information in the second field 320 can be used to "obtain" the software by removing the restrictions on its use. Accordingly, the term "obtain" should be interpreted broadly and does not necessarily mean download via a network. Further, with any of these embodiments, the user (or owner) of the medical image viewer 200 can be charged a fee for obtaining the software.

Once the software is obtained, it can be used to display and/or manipulate the medical image data in the first field 310. For example, if the medical image data is a three-dimensional data set that is captured in the image path between the signal processing and detection component 120 and the reconstruction and 3D rendering component 130, the obtained software can be used to extract a 2D image from the three-dimensional data set (i.e., multi-planer reconstruction ("MPR")), create a 3D image from the data set and view the 3D image from different angles, and apply conventional 2D functions, such as gray-scale remapping, edge enhancement, and speckle reduction, to the 3D image. It should be noted that the obtained software can be used in conjunction with or separate from the medical-image-standard-compliant software running on the medical image viewer 200. Further, the medical-image-standard-compliant software can already allow some types of display and/or manipulation of non-medical-image-standard compliant data, with the obtained software providing additional functionality. Also, the obtained software can contain features other than those used to display and/or manipulate the image data. In one embodiment, the obtained software was not installed or available to the image viewer 200 prior to receiving the medical image file with the information regarding how to obtain the software.

In summary, the embodiments described herein incorporate capabilities and information required for viewing and/or manipulating medical images into the image data file sent to a medical image viewer. These embodiments can be used to allow a user to store medical image data that is not in an industry standard format (such as DICOM) and provide information that can be used to obtain the appropriate software to display and/or manipulate this data. One advantage associated with these embodiments is that they provide a "plug-and-play" like capability for processing medical image data that is not in compliance with the medical image standard. These embodiments find particular use with the DICOM format, in that non-DICOM data (such as large 3D/4D datasets, pre-reconstructed data, or RF data) stored in the DICOM private attribute tag can be viewed and/or manipulated using a DICOM-compliant viewer with software obtained using information stored in the DICOM standard attribute tag. (Data from the Ultrasound Research Interface (URI), which allows a user to capture certain types of data, currently limited to RF or I/Q data, can also be used. In general, non-DICOM data can be any intermediate data from element data to display data.) In this way, if a user attempted to open a DICOM file containing non-DICOM data while on an image review station that had no capability to view and/or manipulate the non-DICOM data, the DICOM data would assist the user (such as by displaying a message instructing him to download the appropriate software) in order to "upgrade" his generic review station to one capable of manipulating (e.g., reconstructing) and viewing the non-DICOM image data. In this way, many (if not all) of the manipulations performed by an ultrasound system on a data set can be performed off-line on another ultrasound system or a workstation without pre-loading the off-line system with software prior to receiving the data set. This allows for a different model for archiving images to be created that moves away from archiving 2D ultrasound images as a simple sequence of video images. Further, these embodiments can be configured such that anyone with a DICOM viewing station can access non-compliant image data irrespective of which manufacturer's system generated the data.

As noted above, each of the embodiments described herein can be used alone or in combination with one another. As also noted above, these embodiments can be used with image modalities other than ultrasound imaging, and the claims should not be limited to any particular type of image modality unless explicitly recited therein. Examples of different types of image modalities that can be used with these embodiments include, but are not limited to, computed tomography (CT), magnetic resonance imaging (MRI), computed radiography, magnetic resonance, angioscopy, color flow Doppler, cystoscopy, diaphanography, echocardiography, fluoresosin angiography, laparoscopy, magnetic resonance angiography, positron emission tomography, single-photon emission computed tomography, x-ray angiography, computed tomography, nuclear medicine, biomagnetic imaging, culposcopy, duplex Doppler, digital microscopy, endoscopy, fundoscopy, laser surface scan, magnetic resonance spectroscopy, radiographic imaging, thermography, and radio fluroscopy.

It is intended that the foregoing detailed description be understood as an illustration of selected forms that the invention can take and not as a definition of the invention. It is only the following claims, including all equivalents, that are intended to define the scope of this invention.

What is claimed is:

1. A method for displaying and/or manipulating medical image data, the method comprising:
   (a) receiving, with a medical image viewer in compliance with a medical image standard and comprising medical-image-standard-compliant software, a file in compliance with the medical image standard, wherein the medical image standard specifies a first field for data not in compliance with the medical image standard and a second field for data in compliance with the medical image standard, wherein the first field of the file comprises medical image data and the second field of the file comprises information that can be used to obtain software to at least one of display and manipulate the medical image data;

(b) with the medical-image-standard-compliant software, reading, from the second field, the information that can be used to obtain software to at least one of display and manipulate the medical image data;

(c) obtaining the software identified by the information in the second field;

(d) performing at least one of the following with the software obtained in (c): displaying the medical image data and manipulating the medical image data;

wherein the medical image standard comprises Digital Imaging and Communications in Medicine (DICOM), and wherein the first field of the medical image standard comprises a DICOM private attribute, and wherein the second field of the medical image standard comprises a DICOM standard attribute.

2. The invention of claim 1, wherein the information in the second field comprises a message instructing a user how to obtain the software to at least one of display and manipulate the medical image data.

3. The invention of claim 1, wherein the information in the second field comprises a link to a network location storing the software to at least one of display and manipulate the medical image data, and wherein the software is obtained in (c) in response to a user selecting the link.

4. The invention of claim 1, wherein the information in the second field identifies a network location storing the software to at least one of display and manipulate the medical image data, and wherein the software is obtained in (c) without user action.

5. The invention of claim 1 further comprising charging a fee to a user for the software to at least one of display and manipulate the medical image data.

6. The invention of claim 1, wherein the medical image data comprises ultrasound data.

7. The invention of claim 1, wherein the medical image data is selected from the group consisting of radio frequency (RF) data, pre-scan converted data, pre-reconstruction data, and a three-dimensional data set.

8. The invention of claim 1, wherein (d) comprises displaying the medical image data.

9. The invention of claim 1, wherein (d) comprises manipulating the medical image data.

10. The invention of claim 1, wherein the file is received by the medical image viewer via one of the following: a network, removable media, and a wireless transmission.

11. A medical image viewer comprising:
a display device;
a processor; and
a storage device storing:

a file in compliance with a medical image standard, wherein the medical image standard specifies a first field for data not in compliance with the medical image standard and a second field for data in compliance with the medical image standard, wherein the first field of the file comprises medical image data and the second field of the file comprises information that can be used to obtain software to at least one of display and manipulate the medical image data;

medical-image-standard-compliant software that, when executed by the processor, is operative to read from the second field, the information that can be used to obtain software to at least one of display and manipulate the medical image data;

wherein the processor is operative to obtain the software identified by the information in the second field and perform at least one of the following with the software identified by the information: displaying the medical image data and manipulating the medical image data;

wherein the medical image standard comprises Digital Imaging and Communications in Medicine (DICOM), and wherein the first field of the medical image standard comprises a DICOM private attribute, and wherein the second field of the medical image standard comprises a DICOM standard attribute.

12. The invention of claim 11, wherein the information in the second field of the file comprises a message instructing a user how to obtain the software to at least one of display and manipulate the medical image data.

13. The invention of claim 11, wherein the information in the second field of the file comprises a link to a network location storing the software to at least one of display and manipulate the medical image data, and wherein the processor obtains the software to at least one of the display and manipulate the medical image data in response to a user selecting the link.

14. The invention of claim 11, wherein the information in the second field of the file identifies a network location storing the software to at least one of display and manipulate the medical image data, and wherein the processor obtains the software to at least one of display and manipulate the medical image data without user action.

15. The invention of claim 11, wherein the medical image data comprises ultrasound data.

16. The invention of claim 11, wherein the medical image data is selected from the group consisting of radio freguency (RF) data, pre-reconstruction data, and a three-dimensional data set.

17. The invention of claim 11, wherein the processor is operative to display the medical image data.

18. The invention of claim 11, wherein the processor is operative to manipulate the medical image data.

19. The invention of claim 11, wherein the file is received by the medical image viewer via one of the following: a network, removable media, and a wireless transmission.

* * * * *